(12) United States Patent
Loubens et al.

(10) Patent No.: US 6,520,979 B1
(45) Date of Patent: Feb. 18, 2003

(54) LINKING DEVICE FOR SURGICAL INSTRUMENT

(76) Inventors: Thierry Loubens, 31 chemin du Monteiller, Saint Didier au Mont d'Or (FR), F-69370; Lionel Riou, 218 avenue Felix Faure, Lyon (FR), F-69003; Christophe Garin, 47 cours Franklin Roosevelt, Lyon (FR), F-69006

( * ) Notice: Subject to any disclaimer, the term of this patent is extended or adjusted under 35 U.S.C. 154(b) by 0 days.

(21) Appl. No.: 09/674,082

(22) PCT Filed: Mar. 2, 1999

(86) PCT No.: PCT/FR99/00458
§ 371 (c)(1),
(2), (4) Date: Jan. 3, 2001

(87) PCT Pub. No.: WO99/55242
PCT Pub. Date: Nov. 4, 1999

(30) Foreign Application Priority Data

Apr. 29, 1998 (FR) ............................................. 98 05690

(51) Int. Cl.7 ............................................. A61B 17/28
(52) U.S. Cl. ...................... 606/205; 606/206; 606/207; 606/208; 606/83
(58) Field of Search ................................ 606/205, 206, 606/207, 208, 79, 83, 170

(56) References Cited

U.S. PATENT DOCUMENTS

| | | | |
|---|---|---|---|
| 4,990,148 A | * 2/1991 | Worrick et al. | 606/83 |
| 5,026,375 A | * 6/1991 | Linovitz et al. | 606/79 |
| 5,273,519 A | * 12/1993 | Koros et al. | 606/83 |
| 5,385,570 A | * 1/1995 | Chin et al. | 606/79 |
| 5,507,774 A | * 4/1996 | Holmes et al. | 606/205 |
| 5,584,844 A | * 12/1996 | Weisshaupt | 606/208 |
| 5,851,214 A | * 12/1998 | Larsen et al. | 606/205 |
| 5,961,531 A | * 10/1999 | Weber et al. | 606/170 |
| 6,126,674 A | * 10/2000 | Janzen | 606/206 |

FOREIGN PATENT DOCUMENTS

| | | |
|---|---|---|
| DE | 4115937 | 5/1992 |
| DE | 4341734 | 9/1994 |
| DE | 29601208 | 3/1996 |
| DE | 29718969 | 3/1998 |
| EP | 0706780 | 4/1996 |

* cited by examiner

Primary Examiner—Rodney M. Lindsey
(74) Attorney, Agent, or Firm—Dowell & Dowell, P.C.

(57) ABSTRACT

The invention concerns a linking device for a surgical instrument (1) comprising an axis of rotation (6) including angular indexing means for limiting the mobile handle (5) travel about the axis (6) in operative position and for extending, in a predetermined position of said indexing means, the mobile handle (5) travel about the axis (6), without having to detach said handle for setting in place or removing the mobile element (8).

32 Claims, 12 Drawing Sheets

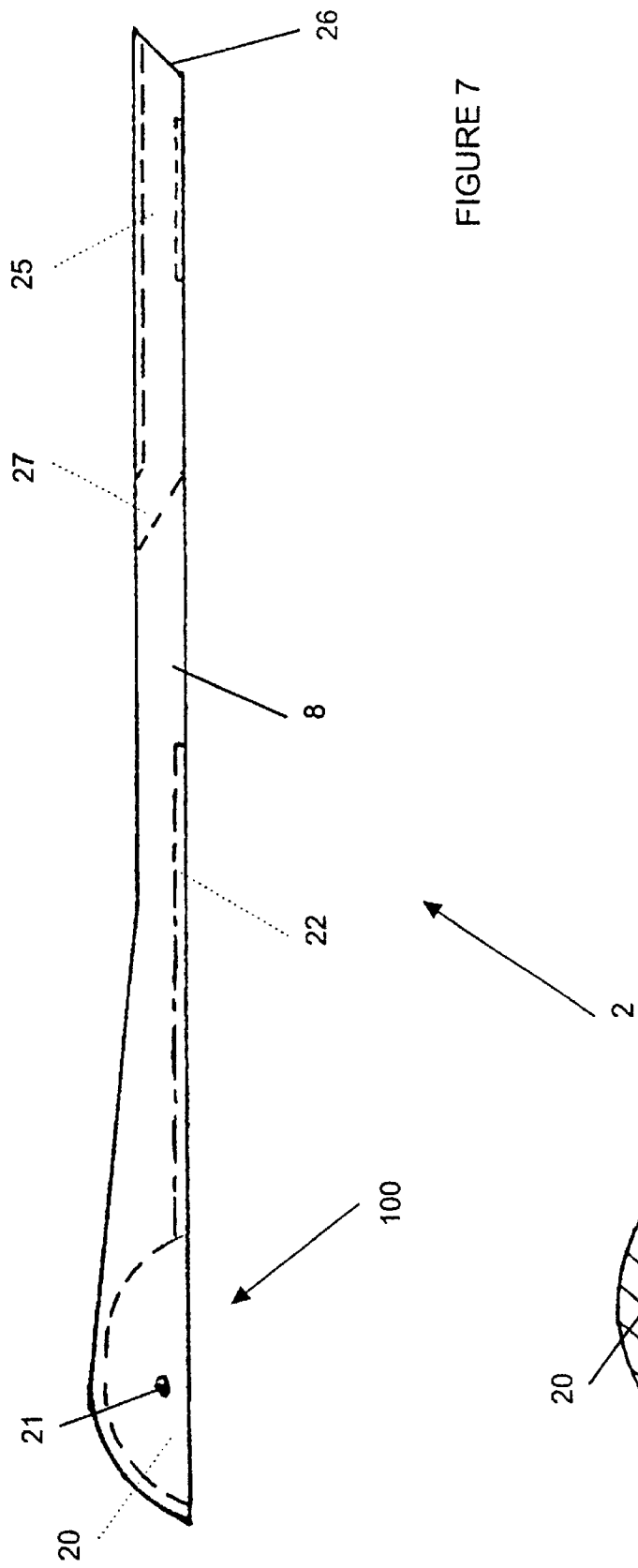
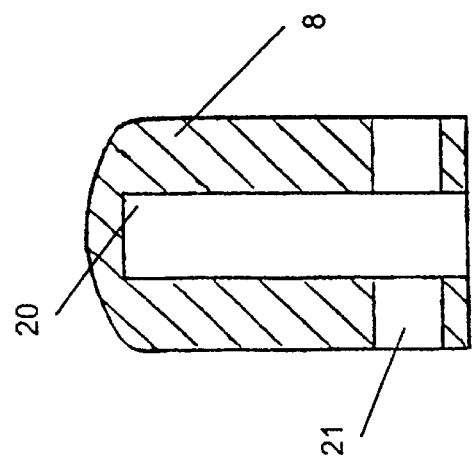

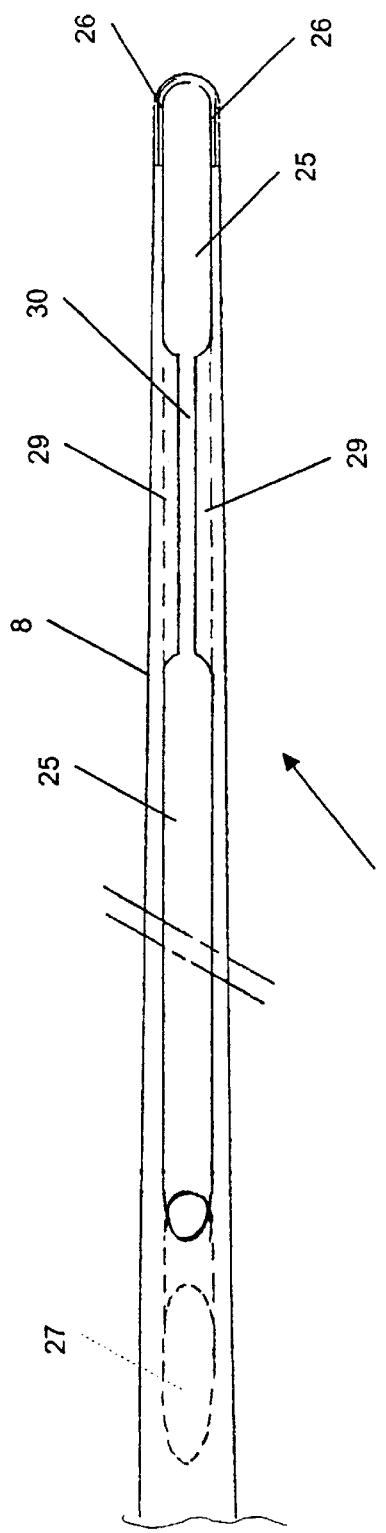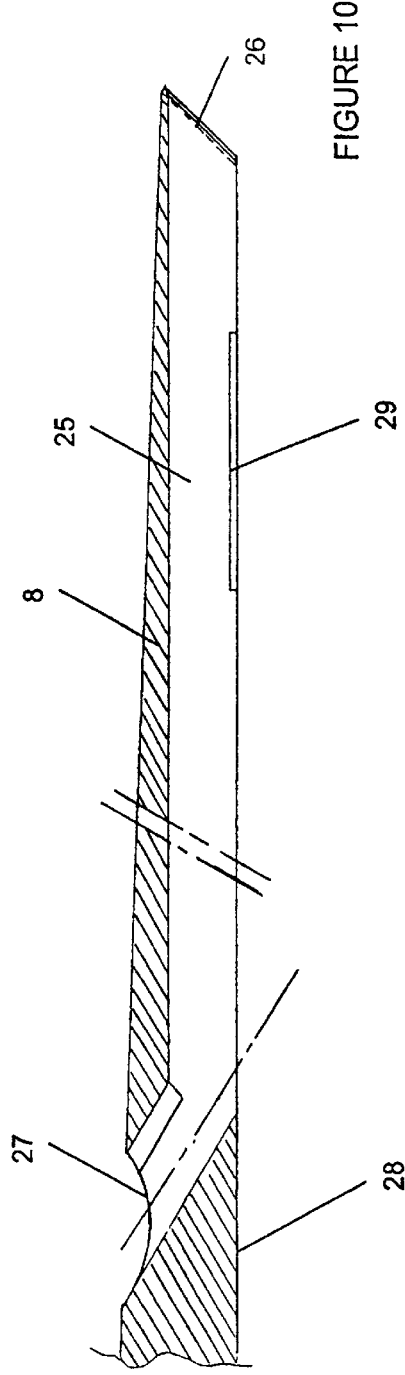

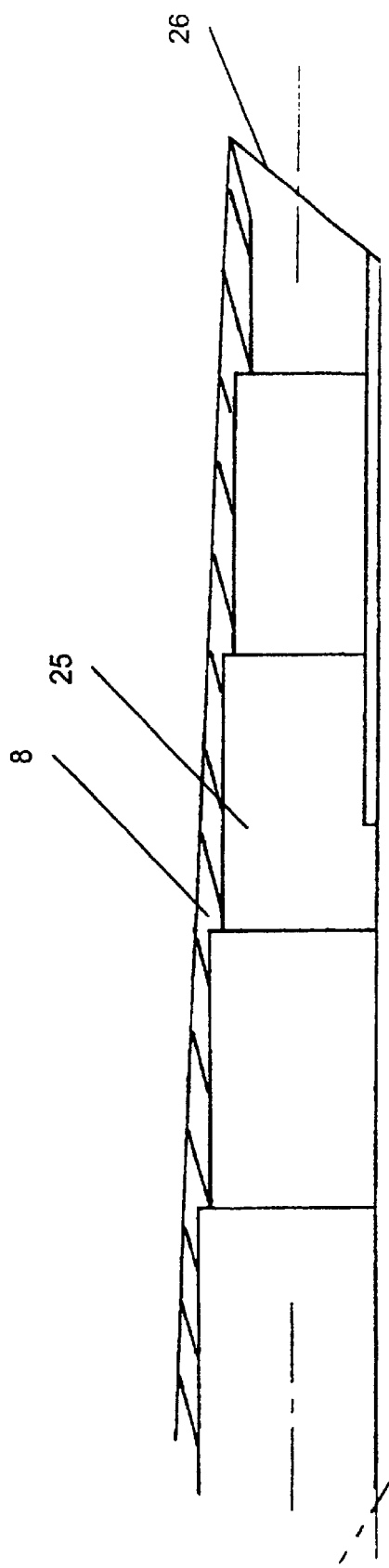
FIGURE 21a
FIGURE 21b
FIGURE 21c

LINKING DEVICE FOR SURGICAL INSTRUMENT

The present invention relates to a connecting device for the rapid positioning or withdrawal of one of the elements constituting a surgical instrument.

The connecting device is particularly intended for surgical instruments comprising elements that slide relative to one another and that are provided with either cutting means or with gripping means.

The connecting device likewise applies to surgical instruments comprising a fixed element and a mobile element that are actuated by means of a grip.

Patent DE 29718969 has disclosed, for example, a surgical instrument of hollow punch type comprising a main body forming a fixed clamping jaw, a mobile clamping jaw moving on the fixed one by means of an elastically loaded grip.

On the one hand, the mobile grip pivots around an axis of rotation and, on the other hand, is provided with means of elastic return movement connecting said mobile grip to a fixed grip of the main body.

It can be noted that the elastic return movement means limit the travel of the mobile grip around its axis of rotation. The travel of the mobile grip is extended when the elastic return movement means are neutralized to allow the grip to rotate freely around its axis.

The extension of the travel of the mobile grip makes it possible to position the drive means of the mobile clamping jaw in a defined angular position to facilitate either the positioning or the withdrawal of said clamping jaw.

It is known that this type of instrument obligates the surgeon to disassemble the elastic return movement element to be able to withdraw the mobile clamping jaw, which renders the assembly and disassembly of the instrument complicated.

When disassembling the elastic return movement means it can also be noted that the mobile grip is not kept on its axis of rotation and that inadvertently it can be disassembled or knocked down when withdrawing or positioning the mobile element.

This situation can complicate the assembly or the disassembly of the instrument by the surgeon when he is at the operating table.

It is these disadvantages, in particular, that the present invention intends to remedy.

The connecting device for a surgical instrument according to the present invention has the aim to allow the rapid assembly and disassembly of the mobile element, without having to withdraw the axis of rotation or other components of the instrument.

The connecting device according to the present invention also makes it possible to convert the rotary movement into a translational movement for the sliding of one of the elements relative to the other fixed element.

A connecting device for a surgical instrument comprising a fixed element extended by a fixed grip, an axis of rotation around which pivots a mobile grip for the drive of a mobile element in a longitudinal displacement with respect to the fixed element, and elastic means making possible the return movement of the mobile grip with respect to the fixed grip, characterized by the fact that the axis of rotation comprises angular indexing means elastically loaded by means of a spring in order to make it possible, on the one hand, to limit the travel of the mobile grip around the axis in its operating position and, on the other hand, to extend, in a position defined by said indexing means, the travel of the mobile grip around the axis without the dismantling of said grip to permit the positioning or the withdrawal of the mobile element.

A connecting device characterized in that the angular indexing devices are constituted by a nut solidly affixed to an indexing finger, which nut interacts with a screw elastically loaded by a spring so that the nut and screw assembly constitutes the axis of rotation of the surgical instrument.

A connecting device characterized in that the indexing finger of the nut is disposed on a surface parallel to the one bearing the axis of rotation and comprises an elongated section to limit the rotation of the grip in the operating position of the instrument.

A connecting device characterized in that the mobile grip possesses a curved profile, of which one of the arms is extended by a plate that passes through an aperture practiced within the thickness of the main body of the surgical instrument to interact with the mobile element.

A connecting device characterized in that the plate is pierced by a borehole interacting with the axis of rotation of the mobile grip and that it is provided with a notch intended to house a spindle of the mobile element.

A connecting device characterized in that the aperture possesses a conical profile delimited by inclined surfaces.

A connecting device characterized in that the screw comprises a tightening head solidly affixed to a cylindrical body, of which the opposite end from the head is provided with a threaded section.

A connecting device characterized in that the compression spring is disposed around the cylindrical body of the screw so as to bear against the tightening head and the main body of the surgical instrument.

The present invention does also relate to a surgical instrument comprising angular indexing devices of a mobile grip to make possible in a defined position the positioning or the withdrawal of a mobile element.

A connecting device characterized in that the tightening head is solidly affixed parallel to the cylindrical body of a finger, allowing the angular indexing of the axis of rotation.

A connecting device of hollow punch type comprising a main body forming a fixed clamping jaw and a fixed grip, a mobile clamping jaw moving on the fixed one by means of a mobile grip elastically loaded with respect to the fixed grip for its pivoting around an axis of rotation, characterized in that the axis of rotation comprises angular indexing means, elastically loaded by a spring to make it possible, on the one hand, to limit the travel of the mobile grip around the axis of rotation in its operating position and, on the other hand, to extend in a defined position of said indexing means the travel of the mobile grip around the axis without dismantling the grip to facilitate the positioning or the withdrawal of the mobile element.

A surgical instrument characterized in that the angular indexing means are constituted by a nut solidly affixed to an indexing finger, which nut interacts with a screw elastically loaded by a spring, so that the nut and screw assembly constitutes the surgical instrument's axis of rotation.

A surgical instrument characterized in that the indexing finger of the nut is disposed on a surface parallel to the one that bears the axis of rotation and that it comprises an elongated sector to limit the rotation of the grip in the operating position of the instrument.

A surgical instrument characterized in that the mobile grip possesses a curved profile, of which one of its prongs is extended by a plate that passes through an aperture practiced in the thickness of the main body of the surgical instrument so as to interact with the mobile element.

A surgical instrument characterized in that the plate is pierced by a borehole that interacts with the axis of rotation of the mobile grip and that it is provided with a notch for the housing of an axis of the mobile element.

A surgical instrument characterized in that the aperture possesses a conical profile delimited by inclined surfaces.

A surgical instrument characterized in that the screw comprises a tightening head solidly affixed to a cylindrical body, of which the end opposite from said head is provided with a threaded section.

A surgical instrument characterized in that the compression spring is disposed around the screw's cylindrical body so as to bear against the tightening head and the main body of the surgical instrument.

A surgical instrument characterized in that the tightening head is solidly affixed parallel to the cylindrical body of a finger, allowing the angular indexing of the axis of rotation.

FIGS. 7 to 14 are views showing, in detail, the mobile clamping jaws sliding on the main body of the surgical instrument by means of the connecting device according to the present invention.

FIGS. 21a to 21c are views showing an alternative embodiment of the channel made within the mobile clamping jaw of the instrument.

Figure 1:
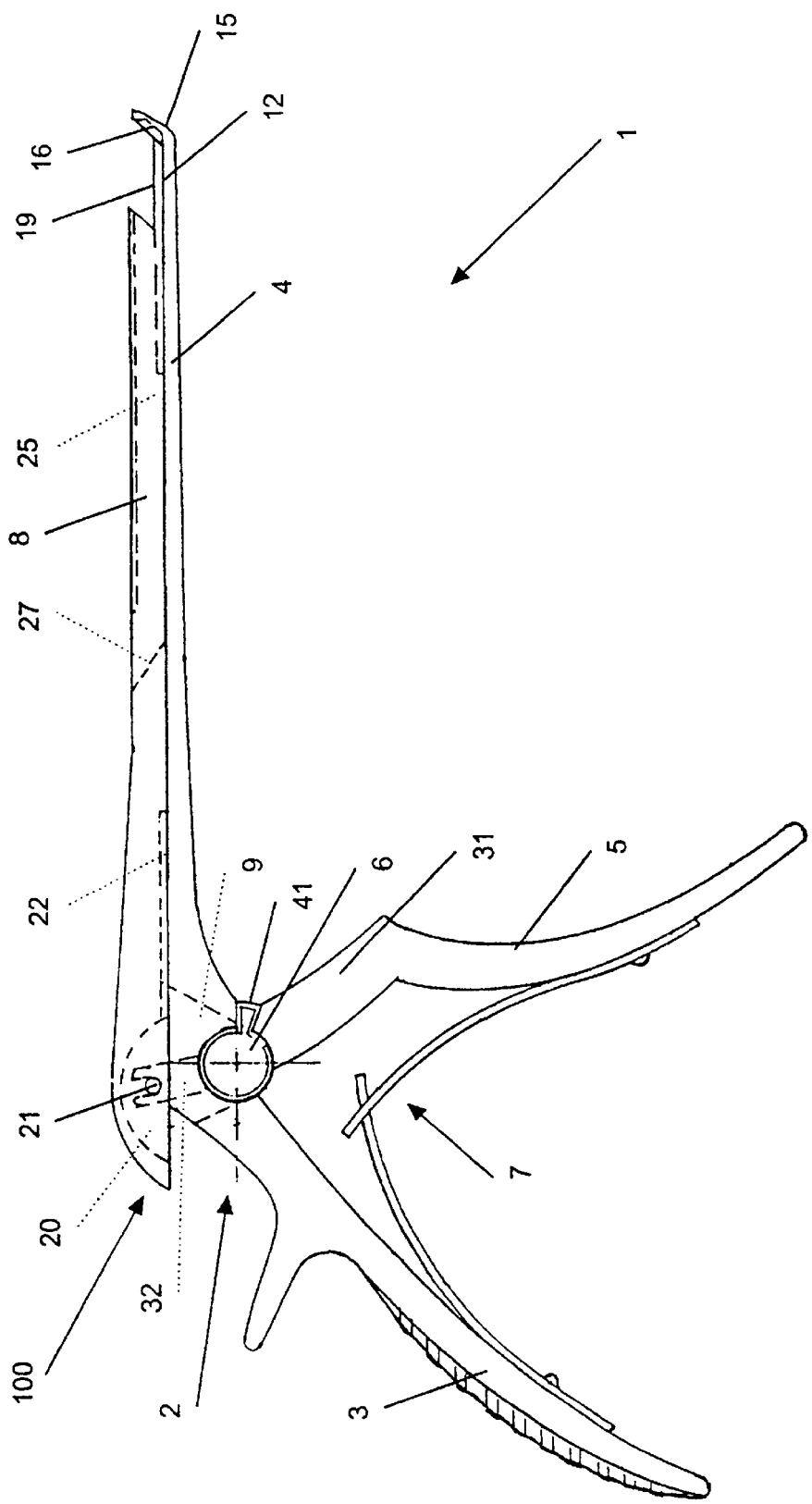
FIG. 1 is a view showing a surgical instrument provided with the connecting device according to the present invention.
Figure 2:
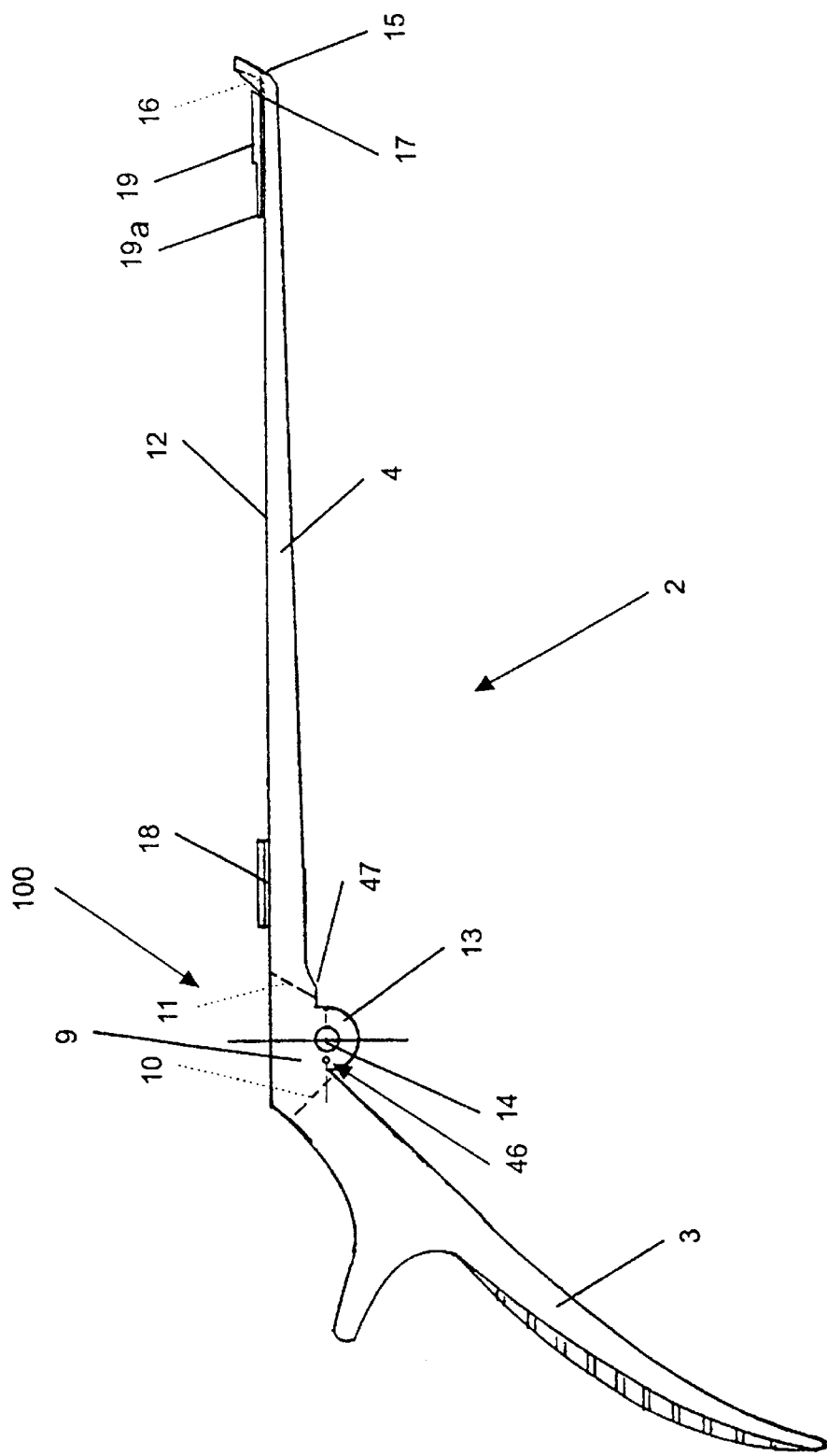
FIGS. 2 to 6 are views showing, in detail, the main body of the surgical instrument for the positioning of the connecting device according to the present invention.

FIG. 1 shows a surgical instrument 1 of the Kerrison forceps type comprising a connecting device 100 permitting, in defined positions, the positioning or the withdrawal of a mobile element or mobile clamping jaw 8.

The surgical instrument 1 comprises a main body 2 formed by a fixed grip 3 which extends in a substantially horizontal plane by way of a fixed element or an elongate support 4 constituting a fixed clamping jaw.

The main body 2 comprises, at the junction between the fixed grip 3 and the fixed clamping jaw 4, a mobile clamping jaw 5 which pivots about a pivot 6, while elastic restoring means 7 are provided between the two grips to place the mobile grip 5 in a position of origin after each pivoting movement.

The fixed clamping jaw 4 of the main body 2 interacts with the mobile element, or mobile clamping jaw 8, which slides in a longitudinal direction from front to rear on the said fixed clamping jaw 4 when a force is applied to the mobile grip 5.

The connecting device 100 is formed by the pivot 6 which comprises angular indexing means making it possible both to limit the travel of the mobile grip about the pivot 6 in the operating position and to extend, in a defined position of the said indexing means, the travel of the mobile grip 5 about the pivot 6 without dismantling of the said grip to permit the positioning or withdrawal of the mobile element or mobile clamping jaw 8.

FIGS. 2 to 6 show, in detail, the main body 2 formed by the fixed grip 3 and the fixed clamping jaw 4.

The main body 2 possesses, within its thickness and at the junction between the grip 3 and the clamping jaw 4, an aperture of conical profile 9 delimited by opposite and inclined surfaces 10, 11 so that the more open side of the said aperture is turned to face the upper edge 12 of the fixed clamping jaw 4.

The main body 2 comprises, on each side of the aperture 9, an arcuate lug 13 which is pierced by a drilled hole 14 intended to receive the pivot 6 for the rotational guidance of the mobile grip 5.

In the vicinity of the drilled hole 14, a second drilled hole 46 of lesser diameter than the drilled hole 14 may be provided, intended to receive a guide element 45 solidly fixed to the pivot 6.

The second drilled hole 46 is disposed on the same longitudinal axis as that bearing the drilled hole 14.

The maximum travel of the mobile grip 5 about the pivot 6 within the aperture 9 of the main body 2 is delimited by the inclined and opposite surfaces 10, 11.

The fixed jaw 4 comprises, towards its free end and opposite to the end through which the aperture 9 passes, a tip 15 extending in a substantially vertical direction, either upwards or downwards relative to the longitudinal axis of the surgical instrument 1.

Figure 5:
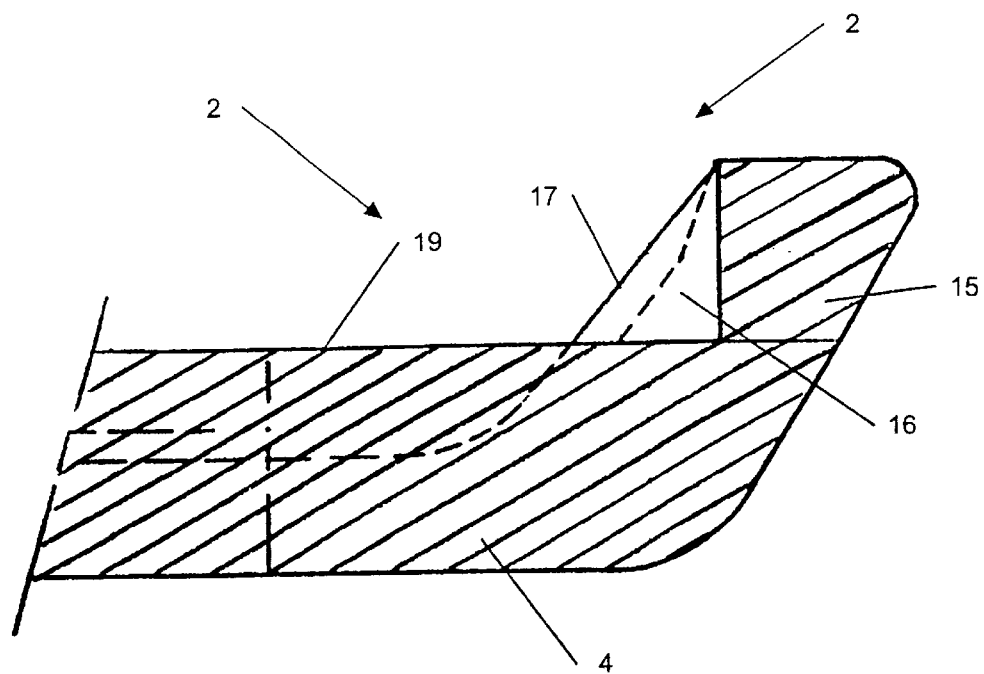

The tip 15 possesses, within its thickness, a hollow 16 delimiting opposite edges 17 which are inclined relative to the upper edge 12 of the fixed clamping jaw 4. The edges 17 of the tip 15 are machined to constitute cutting elements in order to cut bone fragments (FIG. 5).

Figure 6:
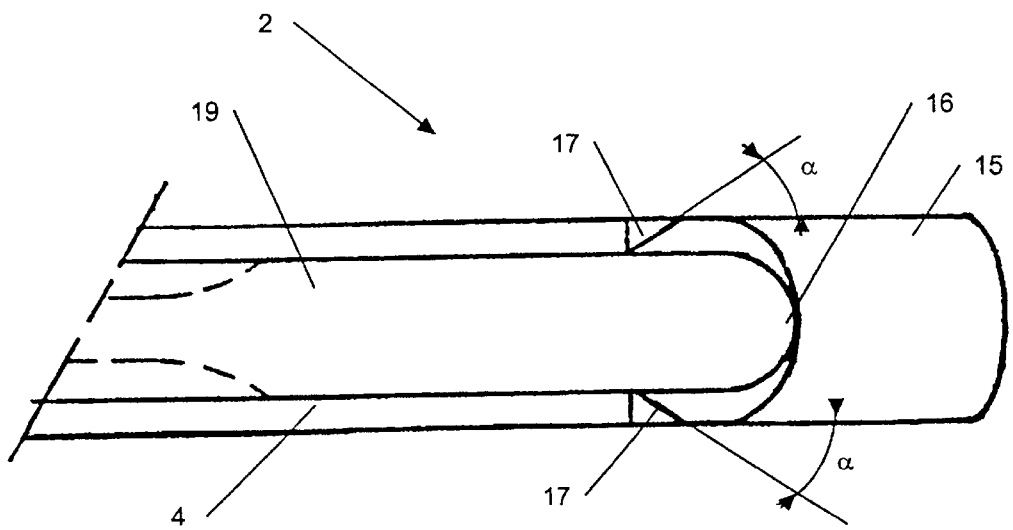

The opposite edges 17 of the tip 15 are chamfered outwards at an angle $\alpha$ of between 15 and 30 degrees relative to the outer edge of the said tip (FIG. 6).

In an alternative embodiment, the tip 15 may possess a rib 16 comprising opposite edges 17 which are inclined outwards and opposite edges (not referenced) which are inclined towards the rib. In this embodiment, the inclination of the angle $\alpha$ is different and adapted to the inclination of the opposite edges facing the interior of the rib 16.

Figure 3:
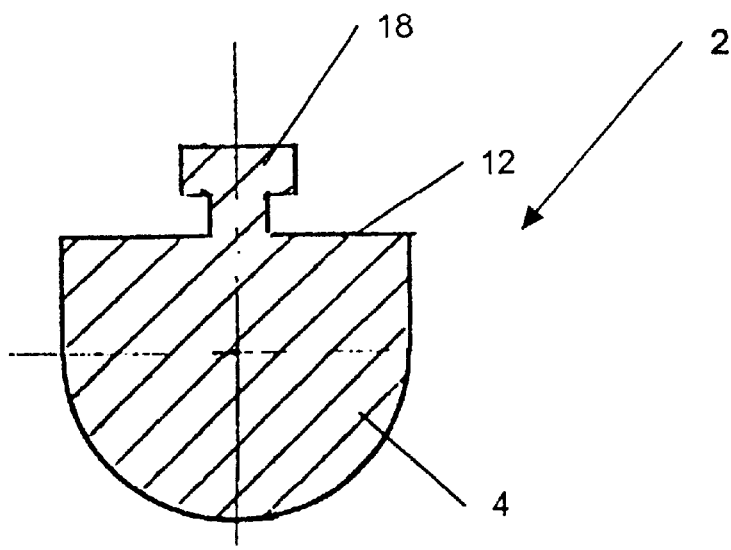
Figure 4:
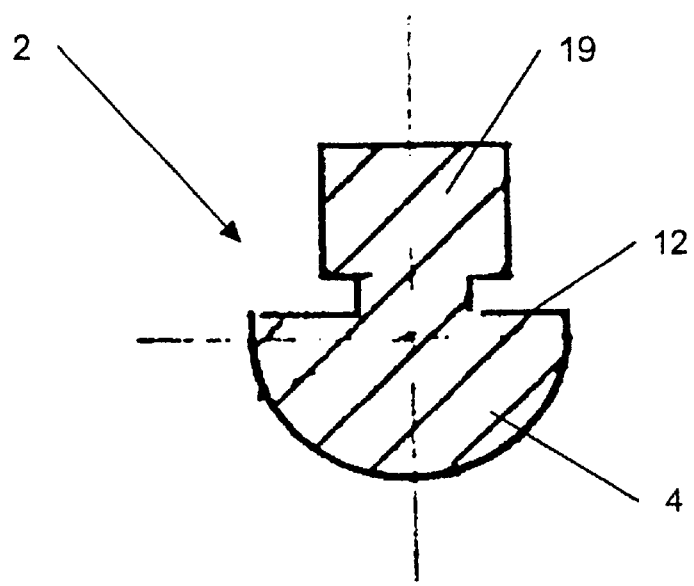

The fixed clamping jaw 4 is solidly fixed, or, its upper edge 12 and opposite the tip 15, to a T-shaped peg 18 permitting the longitudinal guidance of the mobile clamping jaw 8. Similarly, the fixed clamping jaw 4 comprises, in the vicinity of the tip 15, another T-shaped peg 19 which improves the guidance of the mobile clamping jaw 8 over the entirety of its travel (FIGS. 3, 4).

Furthermore, the T-shaped peg 19 comprises, towards the peg 18, a portion 19a of a height less than that envisaged for the peg 19.

Figure 19:
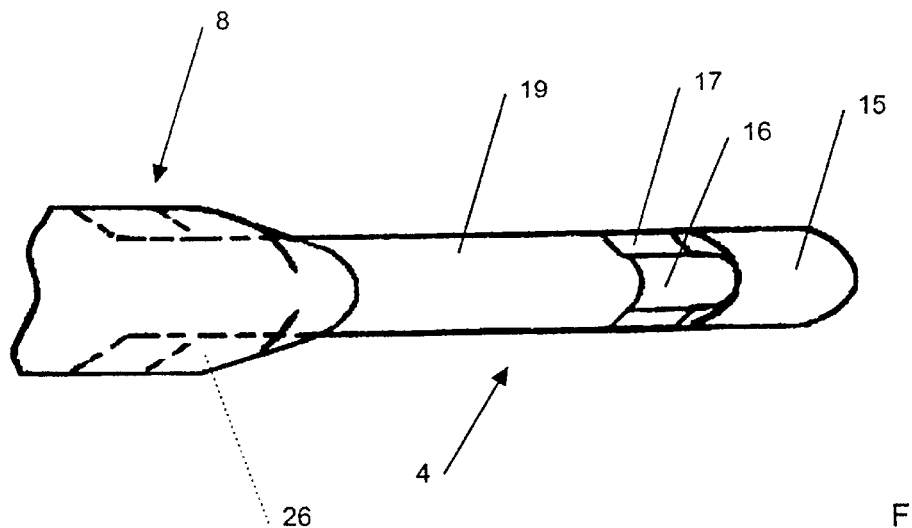
FIGS. 19 and 20 are views showing an alternative embodiment of the fixed clamping jaw illustrated in FIGS. 5 and 6, in that it possesses a reduced width to facilitate engagement into the operating site.
Figure 20:
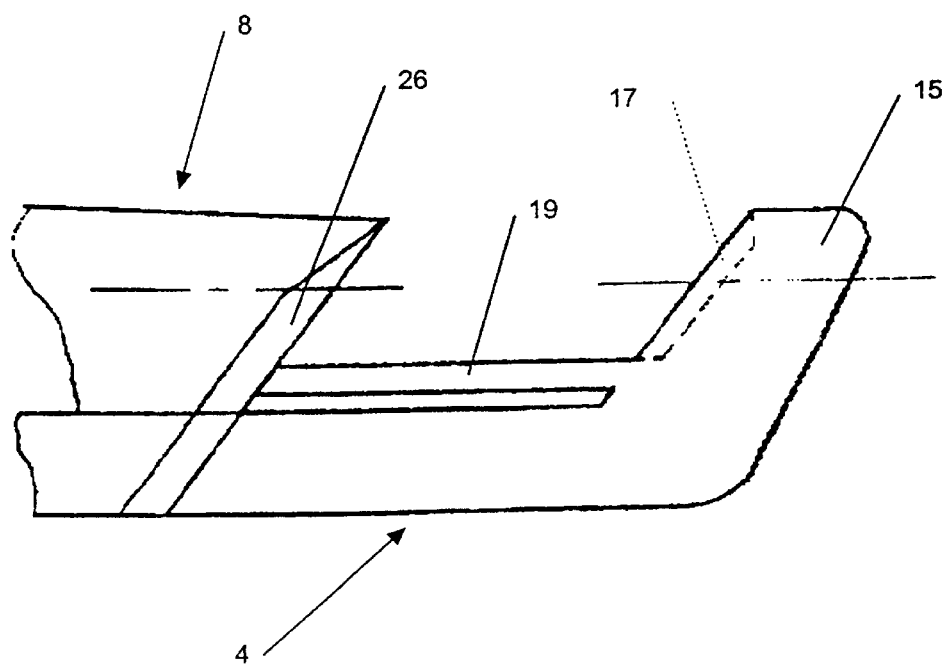

It may be noted that the fixed clamping jaw 4 may possess, in the vicinity of its tip 15, a narrow profile in order to facilitate its introduction into the operating site (FIGS. 19 and 20).

Thus, a position [sic] of the fixed clamping jaw 4 and its tip 15 is reduced in width relative to the rest of the said clamping jaw.

FIGS. 7 to 14 show the mobile clamping jaw 8 which comprises, at one of its ends and within its thickness, an arcuate recess 20. Through this recess passes a spindle 21 which interacts with the mobile grip 5 to transform the rotational movements of the said grip into a linear movement in order for the mobile clamping jaw 8 to slide on the fixed clamping jaw 4.

Figure 8:
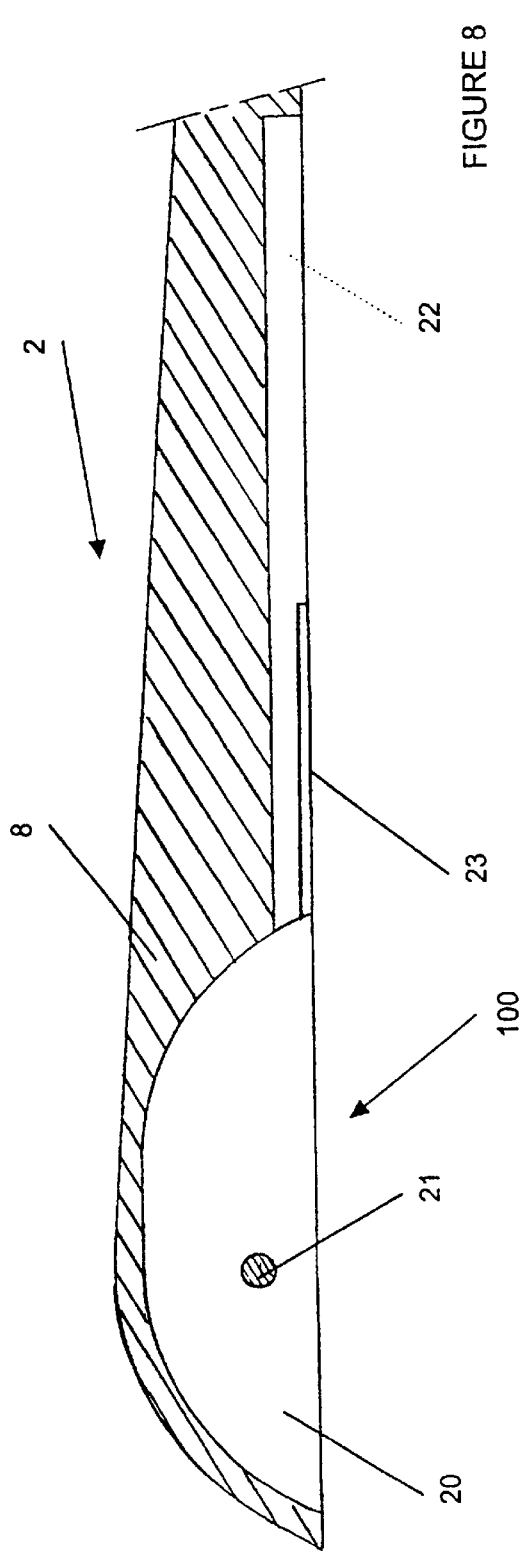
Figure 9:
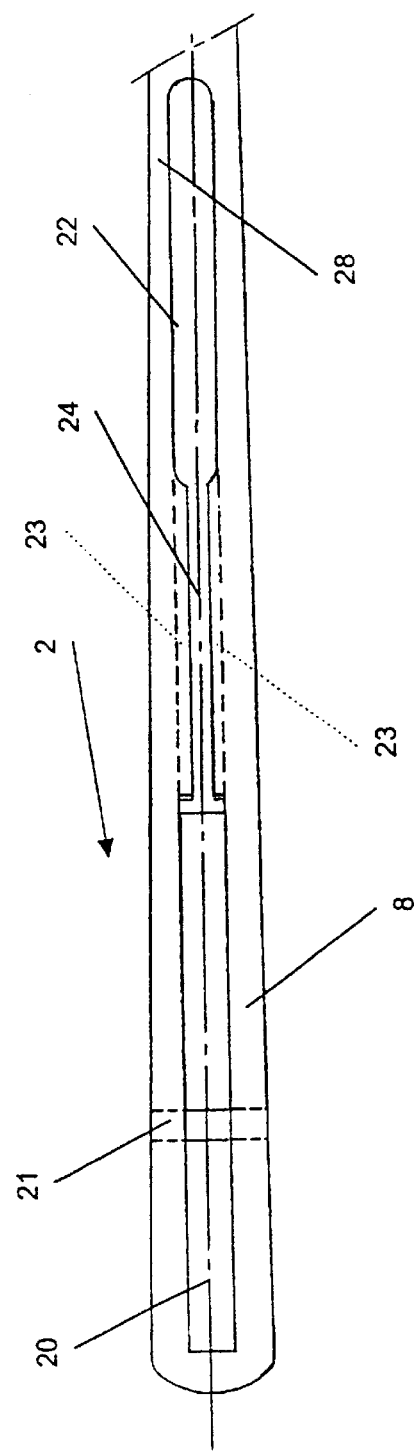

The recess 20 communicates with a groove 22 which extends towards the other end of the mobile clamping jaw 8. The groove 22 comprises, immediately in the extension of the recess 20, opposite ribs 23 separated by an aperture 24 to form a slide which interacts with the T-shaped peg 18 of the fixed clamping jaw 4 (FIGS. 8, 9).

The opposite ribs 23 open into a portion of the groove 22 to form a zone within which the peg 18 is not guided during the movements of the mobile clamping jaw 8.

The latter comprises, in its internal part, a channel 25 opening opposite the recess 20 at an inclined end formed by inclined edges 26 which are machined to possess a cutting profile (FIGS. 10, 11).

Figure 13:
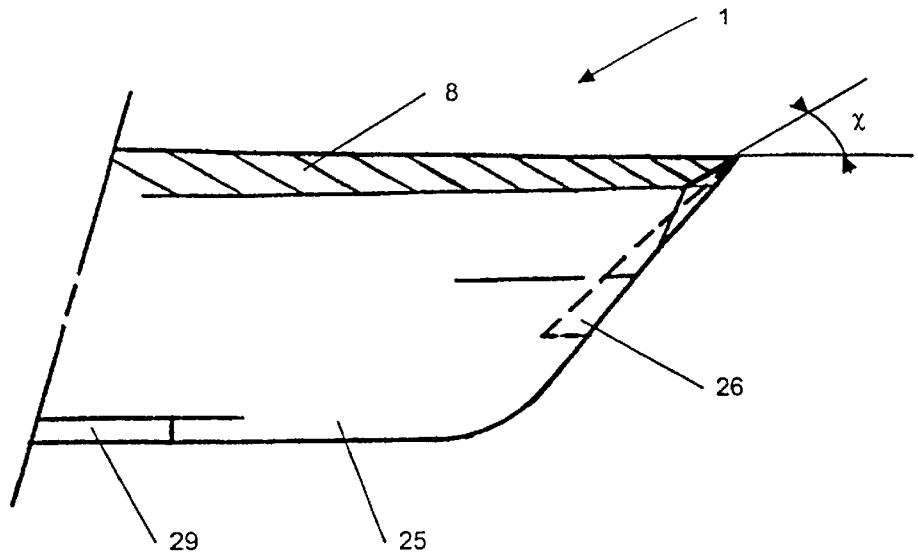
Figure 14:
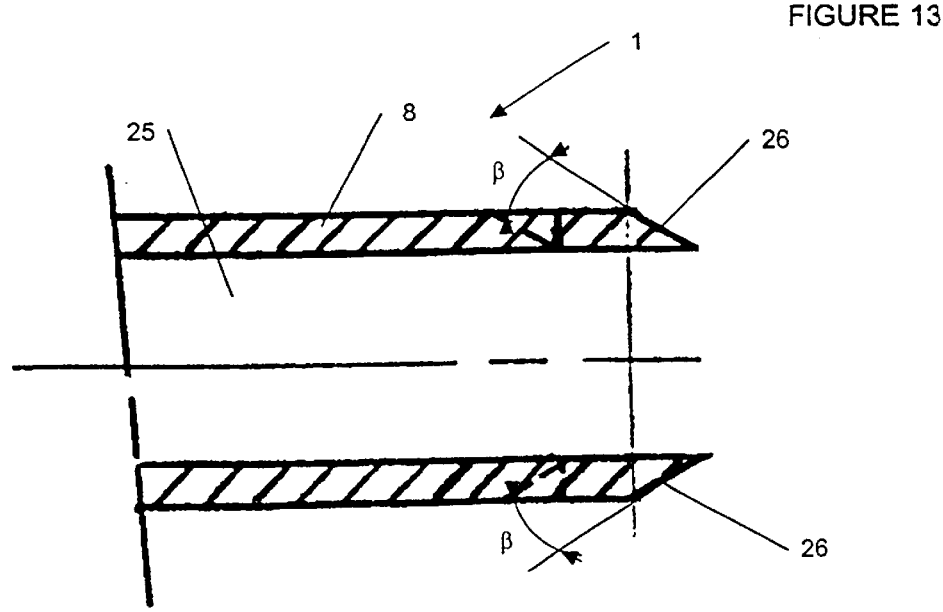

The opposite edges 26 of the inclined end of the mobile clamping jaw 8 are chamfered outwards at an angle β of between 15 and 30 degrees relative to the outer edge of the said clamping jaw (FIGS. 13, 14).

Furthermore, the upper parts of the opposite edges 26 of the mobile clamping jaw 8 are chamfered towards the interior of the channel 25 at an angle χ between 15 and 30 degrees relative to the upper external surface of the said clamping jaw.

The channel 25 extends towards the recess 20 to open outwards and into the upper part of the mobile clamping jaw 8 via an oblong opening 27.

It will be noted that the channel 25 is designed to form a magazine allowing retention of the bone fragments cut away by means of the chamfered edges 17 and 26 of each clamping jaw, both the fixed clamping jaw 4 and the mobile clamping jaw 8.

The channel 25 comprises, in the vicinity of the inclined edges 26 and level with the lower edge 28 of the mobile clamping jaw 8, opposite ribs 29 separated by an aperture 30 so as to form a slideway which interacts with the T-shaped peg 19 of the fixed clamping jaw 4 (FIG. 11).

It may be noted that the channel 25 of the mobile clamping jaw 8 possesses a U-shaped profile which is open towards the lower edge 28.

It will be noted that the channel 25 may possess an internal profile which increases in size from the inclined edges 26 towards the opening 27 in order to avoid blockage of the instrument 1 as a result of the accumulation of elements of bone in the said channel.

Thus, the U-shaped profile of the channel 25 may increase by portions, forming steps within the mobile element 8 (FIGS. 21a to 21c).

Figure 15:
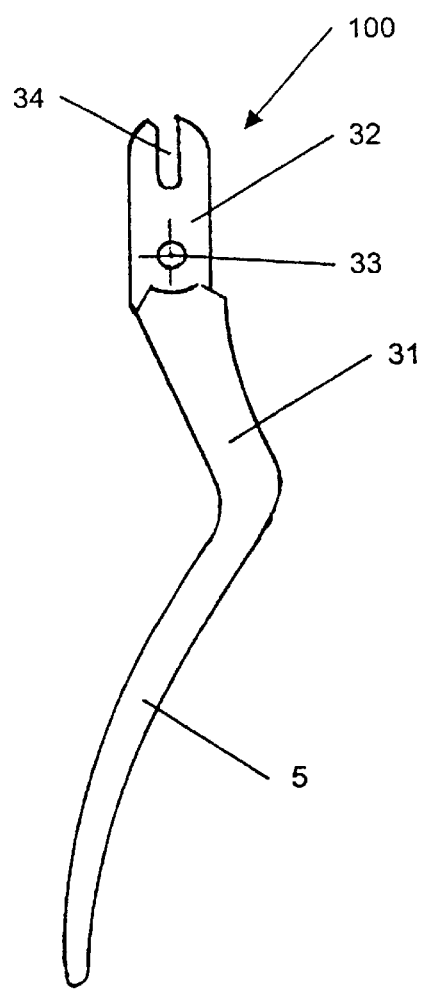
FIG. 15 is a view showing the mobile grip and, more particularly, its plate interacting with the connecting device according to the present invention.

FIG. 15 shows, in detail, the mobile grip 5, which possesses an angled profile formed in part by a short branch 31 extended vertically by a plate 32 which is pierced in the vicinity of the said branch by a drilled hole 33 for the passage of the pivot 6.

The plate 32 comprises, towards its free end, a notch 34 of oblong shape which is designed to interact with the spindle 21 disposed in the recess 20 of the mobile clamping jaw 8.

Figure 16:
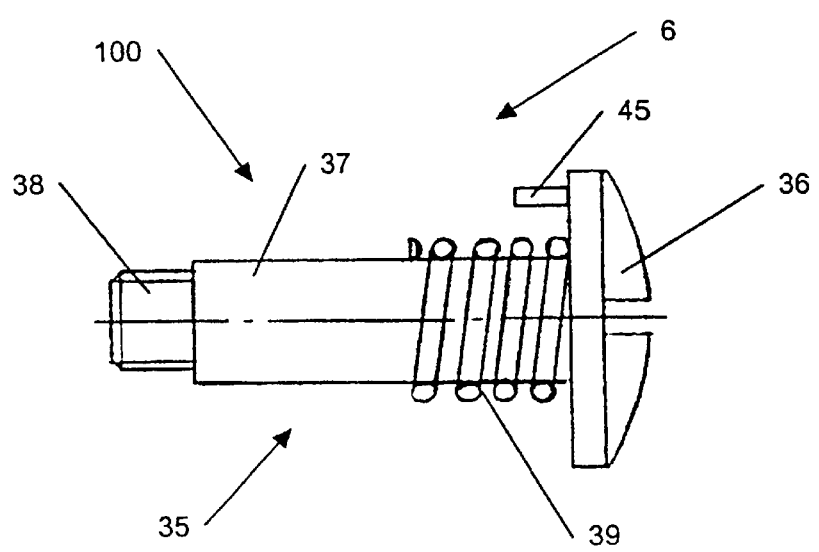
FIGS. 16 to 18 are views showing the connecting device and, more particularly, the pivot allowing the pivoting of the mobile grip on the main body of the instrument.
Figure 18:
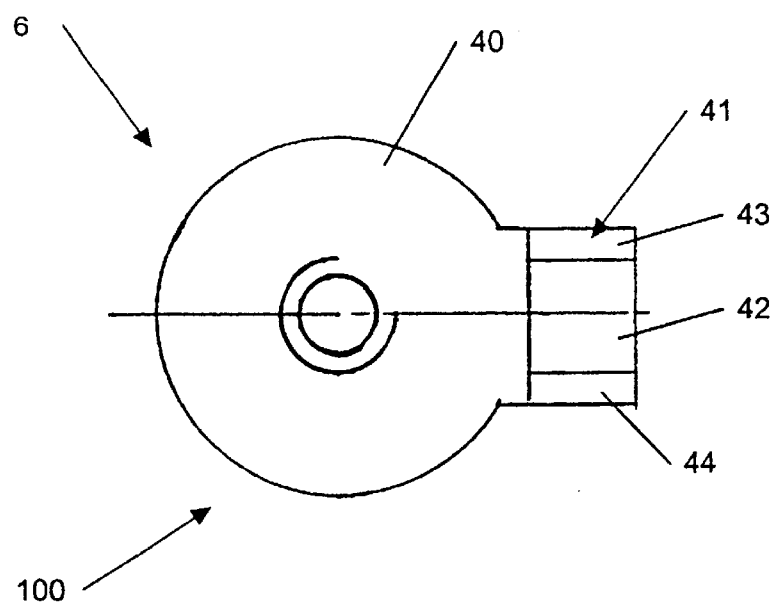
Figure 17:
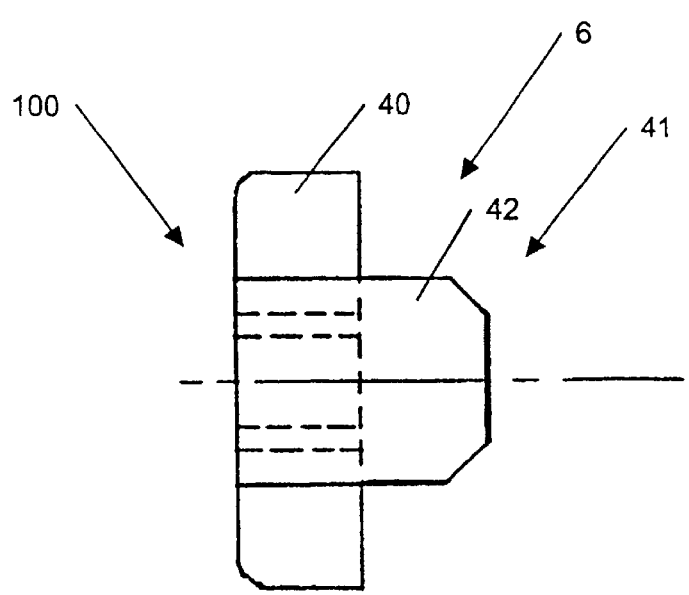

FIGS. 16 to 18 show, in detail, the various elements forming the pivot 6 of the mobile grip 5 of the connecting device 100.

The pivot 6 is formed by a screw 35 possessing a tightening head 36 solidly fixed to a cylindrical body 37 whose end opposite the said head possesses a threaded portion 38.

The tightening head 36 is solidly fixed to a finger 45 extending parallel to the cylindrical body 37. The finger 45 is designed to interact with the drilled hole 46 made in the lug 13 of the main body 2 to permit the translational guidance of the pivot 6.

The finger 45 likewise makes it possible to index, in a defined position, the pivot relative to the main body 2.

A compression spring 39 is disposed around the cylindrical body 37 so as to bear against the tightening head 36 and the main body 2 of the surgical instrument 1.

The pivot 6 comprises a tightening nut 40 which interacts with the threaded portion 38 of the screw 35. The tightening nut 40 comprises, on its periphery, an indexing finger 41 which extends towards the head 36 of the screw 35 when the said nut is screwed onto the said screw. The indexing finger 41 is disposed in a plane parallel to that containing the pivot 6 of the mobile grip 5.

The indexing finger 41 comprises an elongate portion 42 possessing two opposite faces 43, 44 which are inclined in order that the said finger should possess a wedge shape.

The mobile grip 5 is disposed between the two lugs 13 of the main body 2, partly in order that the plate 32 should pass through the aperture 9 and terminate above the upper edge 12 of the fixed clamping jaw 4, and partly in order that the drilled hole 33 of the said plate should be disposed at the same level as those 14 of each lug 13.

The tightening screw 35 provided with the spring 39 is introduced into the drilled hole 14 of the first lug 13 and then passes through the drilled hole 33 of the plate 32 and the other drilled hole 14 of the second lug 13 to permit the screwing of the nut 40 onto the threaded portion 38 of the cylindrical body 37.

Thus, the spring 39 is compressed between the head 36 of the tightening screw 35 and the outer face of the first lug 13 of the main body 2, while the nut 40 comes to bear against the outer face of the second lug 13.

The tightening nut 40 is tightened on the screw 35 so that the indexing finger 41 is placed between the branch 31 of the mobile grip 5 and a straight shoulder 47 of the fixed clamping jaw 4 of the main body 2.

The indexing finger 41 and more particularly the elongate portion 42 bears against the branch 31 and the straight shoulder 47 to limit the travel of the mobile grip 5 about its pivot 6 in order to prevent the plate 32 being in the immediate vicinity of the inclined surface 10 of the aperture 9.

The positioning of the mobile clamping jaw 8 on the fixed clamping jaw 4 can only be undertaken if the plate 32 of the mobile grip 5 comes into the immediate vicinity of the inclined surface 10 of the aperture 9.

For this, it is therefore necessary to apply pressure to the head 36 of the screw 35 of the pivot 6 in order to compress the spring 39 and release the elongate portion 42 of the indexing finger 41 of the nut 40 from its position of origin between the branch 31 and the shoulder 47.

As soon as the portion 42 is withdrawn from its position of origin, the mobile grip 5, under the pressure of the elastic restoring means 7, can pivot through a few additional degrees about its pivot 6 in order to extend its travel.

In this position, the plate 32 of the grip 5 is placed in the immediate vicinity of the inclined surface 10 so that the notch 34 faces the rear of the main body 2, so as to free its access. The position of the plate 32 permits the introduction of the spindle 21, passing through the recess 20 of the mobile clamping jaw 8 into the notch 34.

Simultaneously with the positioning of the spindle 21 in the notch 34, the T-shaped peg 18 of the fixed clamping jaw 4 is seated in the portion of the groove 22 more remote from the recess 20 of the mobile clamping jaw 8, while the peg 19 interacts with the channel 25 provided towards the inclined end of the said mobile clamping jaw.

It is then sufficient to apply light pressure to the mobile grip 5, compressing the elastic restoring means 7, for it to pivot about the pivot 6, permitting the return of the indexing finger 41 into its position of origin under the action of the spring 39, in other words for the portion 42 once again to bear against the branch 31 and the shoulder 47.

The rotation of the grip 5 about the pivot 6 makes it possible for the mobile clamping jaw 8 to be driven in a translational movement on the fixed clamping jaw 4 in order for the pegs 18 and 19 to come into contact with the ribs 23 and 29, respectively, to ensure the guidance of the said mobile clamping jaw during its sliding movements on the fixed clamping jaw 4.

Likewise, the return of the pivot 6 and of its indexing finger 41 to its position of origin under the action of the spring 39 prevents the plate 32 of the grip 5 from coming into the vicinity of the inclined surface 10 of the aperture 9. This position makes it possible to limit the rotation of the grip about the pivot 6, and thus to limit the translational movement of the mobile clamping jaw 8 on the fixed clamping jaw 4 to prevent the said mobile clamping jaw escaping from the main body 2.

Thus, the mobile clamping jaw 8 is retained in the operating position on the main body 2 of the instrument 1 and may undergo a translational movement on the fixed clamping jaw 4 by means of the mobile grip 5 when the latter pivots about its pivot 6.

In operation, the connecting device 100 permits, by the agency of the mobile grip 5, the movement of the mobile clamping jaw 8 on the fixed clamping jaw 4, between an open position where the chamfered edges 17 and 26 are remote from one another and a closed position where the chamfered edges 17 and 26 bear upon one another.

The open position of the clamping jaws 4 and 8 is obtained when the mobile grip 5 is at rest, in other words when the branch 31 bears on the elongate portion 42 of the indexing finger 41 of the nut 40.

The closed position of the clamping jaws 4 and 8 is obtained when the mobile grip 5 is driven in rotation about its pivot 6 until the plate 32 comes into the immediate vicinity of the inclined surface 11 of the aperture 9.

It will be noted that the grip 5 is automatically restored to its position of rest, specifically when the clamping jaws 4 and 8 are opened by the agency of the elastic restoring means 7 provided between the said mobile grip 5 and the fixed grip 3 of the main body 2.

The transition of the clamping jaws 4 and 8 from the open to the closed position permits the surgeon to cut away bone pieces or fragments from a body by means of the chamfered edges 17, 26 to provide a passage.

The bone pieces cut away during the successive movements of the mobile clamping jaw 8 on the fixed clamping jaw 4 are recovered in the channel 25 to prevent their falling amid the site of the operation.

The profile of the peg 19, having a portion 19a of reduced height, makes it possible to avoid the accumulation within the channel 25 of pieces of tissue cut away by the chamfered edges 17, 26.

When the channel 25 is full of bone fragments, it is possible to extract them through the oblong opening 27 made in the upper portion of the mobile clamping jaw 8.

The connecting device 100 permits the mobile clamping jaw 8, in a defined position of the indexing means, to be withdrawn from the main body 2 for cleaning or for the recovery of the bone fragments in the same manner as described above for its positioning.

Specifically, it is sufficient to apply pressure on the head 36 of the screw 35 of the pivot 6 in order to compress the spring 39 and release the elongate portion 42 of the indexing finger 41 of the nut 40 from its position of origin between the branch 31 and the shoulder 47.

As soon as the portion 42 is withdrawn from its position of origin, the mobile grip 5, under the pressure of the elastic restoring means 7, can pivot through a few additional degrees about its pivot 6 in order to extend its travel.

In this position, the plate 32 of the grip 5 is placed in the immediate vicinity of the inclined surface 10 so that the notch 34 faces the rear of the main body 2, so as to free its access. The position of the plate 32 allows the withdrawal of the spindle 21 from the recess 20 of the notch 34 and the simultaneous release of the ribs 23 and 29 and pegs 18 and 19 for the withdrawal of the mobile clamping jaw 8 of the main body 2.

It will be noted that the connecting device 100 permits the positioning or withdrawal of the mobile clamping jaw 8 without the dismantling of the mobile grip 5 and of the restoring means 7.

It may be noted that the connecting device 100 according to the present invention may be provided on other surgical instruments in order to permit, in a defined position, the positioning or the withdrawal of one of the elements and, more particularly, the mobile element of the said instrument.

What is claimed is:

1. A connecting device for a surgical instrument (1) comprising a main body with a fixed element (4) that is extended by a fixed grip (3), an axis of rotation (6) around which pivots a mobile grip (5) for the bringing about of a longitudinal movement of a mobile element (8) with respect to the fixed element (4) and elastic means (7) that make possible a return movement of the mobile grip (5) with respect to the fixed grip (3), characterized in that the axis of rotation (6) comprises angular indexing means (40, 41) elastically loaded by a spring (39) so as to make possible, on the one hand, to limit the travel of the mobile grip (5) around the axis (6) in an operating position and, on the other hand, to extend in a defined position of said indexing means the travel of the mobile grip (5) around the axis (6), without disassembling said grip, to permit the positioning or the withdrawal of the mobile element (8).

2. A connecting device in accordance with claim 1, characterized in that the angular indexing means are constituted by a nut (40) solidly affixed to an indexing finger (41), said nut interacting with a screw (35), elastically loaded by said spring (39), so that the nut (40) and screw (35) assembly constitutes the axis of rotation (6) of the surgical instrument (1).

3. A connecting device in accordance with claim 2, characterized in that the indexing finger (41) of the nut (40) is disposed on a surface parallel to the one bearing the axis of rotation (6) and that it is provided with an elongated section (42) to limit the rotation of the grip (5) in the operating position of the instrument (1).

4. A connecting device in accordance with claim 1, characterized in that the mobile grip (5) possesses a curved profile of which one prong (31) is extended by a plate (32) that passes through an aperture (9) practiced in the thickness of the main body (2) of the surgical instrument (1) so as to interact with the mobile element (8).

5. A connecting device in accordance with claim 4, characterized in that the plate (32) is pierced by a borehole (33) interacting with the axis of rotation (6) of the mobile grip (5) and that it is provided with a notch (34) intended to house a spindle (21) of the mobile element (8).

6. A connecting device in accordance with claim 5, characterized in that the aperture (9) possesses a conical profile delimited by inclined surfaces (10, 11).

7. A connecting device in accordance with claim 2, characterized in that the screw (35) comprises a tightening head (36) solidly affixed to a cylindrical body (37) of which the end opposite from said head is provided with a threaded section (38).

8. A connecting device in accordance with claim 7, characterized in that the spring (39) is disposed around the screw's (35) cylindrical body (37) so as to bear against the tightening head (36) and the main body (2) of the surgical instrument (1).

9. A connecting device in accordance with claim 7, characterized in that the tightening head (36) is solidly affixed parallel to the cylindrical body (37) of a finger (45) making possible the angular indexing of the axis of rotation (6).

10. A surgical instrument of hollow punch type comprising a main body (2) constituting a fixed clamping jaw (4) and a fixed grip (3), a mobile clamping element (8) that moves on the fixed jaw (4) by means of a mobile grip (5) that is elastically loaded with respect to the fixed grip (3) for its pivoting around an axis of rotation (6), characterized in that the axis of rotation (6) comprises angular indexing means (40, 41) elastically loaded by a spring (39) so as to make it possible, on the one hand, to limit the travel of the mobile grip (5) around the axis (6) in an operating position and, on the other hand, to extend in a defined position of said indexing means the travel of the mobile grip (5) around the axis (6) without disassembling said grip to facilitate the positioning or the withdrawal of the mobile element (8).

11. A surgical instrument in accordance with claim 10, characterized in that the angular indexing means are constituted by a nut (40) solidly affixed to an indexing finger (41), which nut interacts with a screw (35) elastically loaded by said spring (39) so that the nut (4) and screw (35) assembly constitutes the axis of rotation (6) of the surgical instrument (1).

12. A surgical instrument in accordance with claim 11, characterized in that the indexing finger (41) of the nut (40) is disposed on a surface parallel to the one bearing the axis of rotation (6) and that it comprises an elongated section (42) to limit the rotation of the grip (5) in the operating position of the instrument.

13. A surgical instrument in accordance with claim 10, characterized in that the mobile grip (5) possesses a curved profile of which one prong (31) is extended by a plate (32) that passes through an aperture (9) practiced in the thickness of the main body (2) of the surgical instrument (1) to interact with the mobile element (8).

14. A surgical instrument in accordance with claim 13, characterized in that the plate is pierced by a borehole (33) interacting with the axis of rotation (6) of the mobile grip (5) and that it is provided with a notch (34) intended to house a spindle (21) of the mobile element (8).

15. A surgical instrument in accordance with claim 13, characterized in that the aperture (9) possesses a conical profile delimited by inclined surfaces (10, 11).

16. A surgical instrument in accordance with claim 11, characterized in that the screw (35) is provided with a tightening head (36) solidly affixed to a cylindrical body (37) of which the end opposite from said head is provided with a threaded section (38).

17. A surgical instrument in accordance with claim 16, characterized in that the compression spring (39) is disposed around the cylindrical body (37) of the screw (35) so that It bears against the tightening head (36) and the main body (2) of the surgical instrument (1).

18. A surgical instrument in accordance with claim 16, characterized in that the tightening head (36) is solidly affixed parallel to the cylindrical body (37) of a finger (45) allowing the angular indexing of the axis of rotation (6).

19. A surgical instrument in accordance with claim 10, characterized in that the fixed clamping jaw (4) comprises a tip (15) provided with a hollow (16), defining opposing edges (17) of chamfered profile.

20. A surgical instrument in accordance with claim 19, characterized in that the opposing edges (17) of the tip (15) are chamfered towards the outside at an angle α with respect to an outer edge of said tip.

21. A surgical instrument in accordance with claim 20, characterized in that the angle α is comprised between 15 and 30 degrees with respect to the outer edge of the tip (15).

22. A surgical instrument in accordance with claim 10, characterized in that the mobile clamping element (8) comprises an internal channel delimiting, at the end of said mobile clamping element, opposite edges (26) of chamfered profile.

23. A surgical instrument in accordance with claim 22, characterized in that the opposite edges (26) of the mobile clamping element (8) are chamfered towards the outside at an angle β with respect to the outer edge of said mobile clamping element.

24. A surgical instrument in accordance with claim 22, characterized in that the opposite edges (26) of the mobile clamping element (8) are chamfered towards the inside of the channel (25) at an angle X with respect to the upper edge of said mobile clamping element.

25. A surgical instrument in accordance with claim 23, characterized in that the angle β is a 30° angle with respect to the outer edge of the mobile clamping element (8).

26. A surgical instrument in accordance with claim 24, characterized in that the angle X is a 30° angle with respect to the upper edge of the mobile clamping element (8).

27. A surgical instrument in accordance with claim 10, characterized in that the fixed clamping jaw (4) is provided on its upper edge (12) and in the proximity of an aperture in the main body (9) with a T-shaped peg (18) for the translational guiding of the mobile clamping element (8).

28. A surgical instrument in accordance with claim 19, characterized in that the fixed clamping jaw (4) is provided on its upper edge (12) and in the proximity of the tip (15) with a T-shaped peg (19) for the translational guiding of the mobile clamping element (8).

29. A surgical instrument in accordance with claim 28, characterized in that the T-shaped peg (19) comprises a section (19a) having a height lower than the one designed for the peg.

30. A surgical instrument in accordance with claim 22, characterized in that the mobile clamping element (8) is provided at one of its ends with an arcuate recess (20) traversed by a spindle (21) and extended by a groove (22) provided with opposite ribs (22) separated by an aperture (24) to constitute a first slide, while the other end of the mobile clamping element (8) comprises an inner channel (25) delimiting the chamfered edges (26) and presenting on the side of the lower edge (28) opposite ribs (29) separated by an aperture (30) to constitute a second slide.

31. A surgical instrument in accordance with claim 19, characterized in that the fixed clamping jaw (4) is provided with a narrow section defining a profile of the tip (15).

32. A surgical instrument in accordance with claim 22, characterized in that the channel (25) possesses an internal U-shaped profile that increases in size from the edges (26) and towards an opening (27).

* * * * *